US008786857B2

(12) United States Patent
Masterson et al.

(10) Patent No.: US 8,786,857 B2
(45) Date of Patent: Jul. 22, 2014

(54) MITIGATION OF OPTICAL SIGNAL NOISE USING A MULTIMODE TRANSMIT FIBER

(75) Inventors: Bernard Patrick Masterson, Louisville, CO (US); James Howell, Louisville, CO (US); Henrik Hofvander, Boulder, CO (US); Andrew D. Sappey, Lakewood, CO (US)

(73) Assignee: Zolo Technologies, Inc., Boulder, CO (US)

( * ) Notice: Subject to any disclaimer, the term of this patent is extended or adjusted under 35 U.S.C. 154(b) by 158 days.

(21) Appl. No.: 13/389,902

(22) PCT Filed: Aug. 10, 2010

(86) PCT No.: PCT/US2010/045077
§ 371 (c)(1),
(2), (4) Date: Feb. 10, 2012

(87) PCT Pub. No.: WO2011/019755
PCT Pub. Date: Feb. 17, 2011

(65) Prior Publication Data
US 2012/0140234 A1 Jun. 7, 2012

Related U.S. Application Data

(60) Provisional application No. 61/232,732, filed on Aug. 10, 2009.

(51) Int. Cl.
*G01N 21/00* (2006.01)
*F23N 5/08* (2006.01)

(52) U.S. Cl.
USPC .............. 356/437; 356/445; 60/772; 431/75; 385/12

(58) Field of Classification Search
USPC .............. 356/432–440, 445–448; 385/12–13; 60/772, 793; 431/75
See application file for complete search history.

(56) References Cited

U.S. PATENT DOCUMENTS

| 3,778,170 A | 12/1973 | Howell et al. |
| 4,011,403 A | 3/1977 | Epstein et al. |

(Continued)

FOREIGN PATENT DOCUMENTS

| CN | 1163665 A | 10/1997 |
| CN | 1343873 | 4/2002 |

(Continued)

OTHER PUBLICATIONS

International Search Report and Written Opinion from PCT/US05/02853, dated Aug. 29, 2005.

(Continued)

*Primary Examiner* — Hoa Pham
(74) *Attorney, Agent, or Firm* — Swanson & Bratschun, L.L.C.

(57) ABSTRACT

An apparatus and methods for measuring combustion parameters in the measurement zone of a gas turbine engine. The measurement zone is defined as being between an outer casing and an engine component having a reflecting surface inside the outer casing. The apparatus comprises a laser generating a transmitting beam of light of a select wavelength and a multimode transmitting fiber optically coupled to the laser. A transmitting optic is optically coupled to the multimode optical fiber for transmitting the beam into the measurement zone. The reflecting surface is configured to provide a Lambertian reflection. A receiving optic is positioned to receive the Lambertian reflection. Means are provided in operative association with the multimode transmitting fiber for averaging modal noise induced signal level variation of light propagating within the multimode transmitting fiber.

20 Claims, 4 Drawing Sheets

(56) References Cited

U.S. PATENT DOCUMENTS

| | | |
|---|---|---|
| 4,028,081 A | 6/1977 | Marcatili |
| 4,305,640 A | 12/1981 | Cullis et al. |
| 4,360,372 A | 11/1982 | Maciejko et al. |
| 4,573,761 A | 3/1986 | McLachlan et al. |
| 4,659,195 A | 4/1987 | D'Amelio et al. |
| 4,672,198 A | 6/1987 | Presby |
| 4,712,888 A | 12/1987 | Brooks |
| 4,790,652 A | 12/1988 | Uneus |
| 4,895,421 A | 1/1990 | Kim et al. |
| 4,915,468 A * | 4/1990 | Kim et al. ............... 385/28 |
| 4,980,763 A | 12/1990 | Lia |
| 4,989,979 A | 2/1991 | Buckman |
| 5,030,000 A | 7/1991 | Kanda |
| 5,042,905 A | 8/1991 | Anjan |
| 5,068,515 A | 11/1991 | van den Bergh et al. |
| 5,291,013 A | 3/1994 | Nafarrate et al. |
| 5,396,506 A | 3/1995 | Ball |
| 5,418,881 A | 5/1995 | Hart, Jr. et al. |
| 5,436,444 A | 7/1995 | Rawson |
| 5,448,071 A | 9/1995 | Mccaul et al. |
| 5,468,239 A | 11/1995 | Tanner et al. |
| 5,477,323 A | 12/1995 | Andrews et al. |
| 5,506,721 A | 4/1996 | Hikami et al. |
| 5,515,158 A | 5/1996 | Heineck |
| 5,553,179 A | 9/1996 | Cryan et al. |
| 5,598,264 A | 1/1997 | Failes |
| 5,621,213 A | 4/1997 | Barshad |
| 5,627,934 A | 5/1997 | Muhs |
| 5,701,376 A | 12/1997 | Shirasaki |
| 5,717,209 A | 2/1998 | Bigman et al. |
| 5,742,715 A | 4/1998 | Boehlke et al. |
| 5,748,325 A | 5/1998 | Tulip |
| 5,774,610 A | 6/1998 | O'Rourke |
| 5,798,840 A | 8/1998 | Beiting |
| 5,802,222 A | 9/1998 | Rasch et al. |
| 5,805,318 A | 9/1998 | Rabinovich et al. |
| 5,813,767 A | 9/1998 | Calabro et al. |
| 5,828,797 A | 10/1998 | Minott |
| 5,841,546 A | 11/1998 | Carangelo et al. |
| 5,841,915 A | 11/1998 | Rabinovich et al. |
| 5,933,000 A | 8/1999 | Bosselmann et al. |
| 5,960,129 A | 9/1999 | Kleinschmitt |
| 5,993,194 A | 11/1999 | Lemelson et al. |
| 6,016,372 A | 1/2000 | Fein et al. |
| 6,018,413 A | 1/2000 | Oka |
| 6,042,365 A | 3/2000 | Chen |
| 6,148,131 A | 11/2000 | Geertman |
| 6,150,661 A | 11/2000 | Mccaul et al. |
| 6,160,255 A | 12/2000 | Sausa |
| 6,169,830 B1 | 1/2001 | Kewitsch et al. |
| 6,297,504 B1 | 10/2001 | Andreou |
| 6,345,134 B1 | 2/2002 | Laming et al. |
| 6,351,587 B1 | 2/2002 | Holland |
| 6,363,190 B1 | 3/2002 | Chen |
| 6,366,355 B1 | 4/2002 | deGroot et al. |
| 6,385,372 B1 | 5/2002 | Yang |
| 6,396,056 B1 | 5/2002 | Lord |
| 6,434,302 B1 | 8/2002 | Fidric et al. |
| 6,455,851 B1 | 9/2002 | Lord et al. |
| 6,510,265 B1 | 1/2003 | Giaretta et al. |
| 6,519,385 B1 | 2/2003 | Green |
| 6,542,679 B2 | 4/2003 | DiGiovanni et al. |
| 6,593,573 B1 | 7/2003 | Mccann et al. |
| 6,678,451 B2 | 1/2004 | Kim et al. |
| 6,701,753 B2 | 3/2004 | Dong et al. |
| 6,766,070 B2 | 7/2004 | Williams et al. |
| 6,791,689 B1 | 9/2004 | Weckström |
| 7,075,629 B2 | 7/2006 | Bonne |
| 7,075,653 B1 | 7/2006 | Rutherford |
| 7,080,504 B2 | 7/2006 | Pais |
| 7,158,552 B2 | 1/2007 | Buchold et al. |
| 7,248,755 B2 | 7/2007 | Sappey et al. |
| 2002/0031737 A1 | 3/2002 | Von Drasek et al. |
| 2002/0158202 A1 | 10/2002 | Webber et al. |
| 2002/0181856 A1 | 12/2002 | Sappey et al. |
| 2003/0067952 A1 | 4/2003 | Tsukiji et al. |
| 2003/0101774 A1 | 6/2003 | Oh et al. |
| 2003/0174325 A1 * | 9/2003 | Zhang et al. ............... 356/318 |
| 2003/0191397 A1 | 10/2003 | Webb |
| 2004/0019283 A1 | 1/2004 | Lambert et al. |
| 2004/0065439 A1 | 4/2004 | Tubel |
| 2004/0160596 A1 | 8/2004 | He et al. |
| 2005/0191755 A1 | 9/2005 | Balbach |
| 2006/0032471 A1 | 2/2006 | Yalin |
| 2006/0087655 A1 | 4/2006 | Augustine et al. |
| 2006/0147166 A1 | 7/2006 | Roba et al. |
| 2006/0157239 A1 | 7/2006 | Ramos |
| 2006/0176486 A1 | 8/2006 | Ho |
| 2006/0243931 A1 | 11/2006 | Haran |
| 2006/0278240 A1 | 12/2006 | Spillman et al. |
| 2007/0133921 A1 | 6/2007 | Haffner |
| 2007/0148478 A1 | 6/2007 | Schmitz |
| 2007/0217744 A1 | 9/2007 | Debut et al. |
| 2007/0296966 A1 | 12/2007 | Benicewicz et al. |
| 2008/0002186 A1 | 1/2008 | Masterson et al. |
| 2008/0074645 A1 | 3/2008 | Sappey |
| 2008/0262359 A1 | 10/2008 | Tearney et al. |
| 2008/0289342 A1 | 11/2008 | Sappey |
| 2009/0002684 A1 | 1/2009 | Sanders |
| 2009/0080054 A1 | 3/2009 | Koyata et al. |
| 2009/0207413 A1 | 8/2009 | Carpenter |
| 2009/0252451 A1 * | 10/2009 | Lagakos et al. ............... 385/13 |
| 2010/0068871 A1 | 3/2010 | Tian et al. |
| 2010/0171956 A1 * | 7/2010 | Sappey et al. ............... 356/432 |
| 2011/0188039 A1 | 8/2011 | Aoyama |
| 2012/0025112 A1 | 2/2012 | Li |

FOREIGN PATENT DOCUMENTS

| | | |
|---|---|---|
| DE | 2730508 A1 | 1/1979 |
| EP | 0766080 A1 | 4/1997 |
| EP | 1205736 A | 5/2002 |
| JP | 63-133035 | 6/1988 |
| JP | 4-251214 | 9/1992 |
| JP | 07-504828 | 6/1995 |
| JP | H09-073020 | 3/1997 |
| JP | 10-301153 | 11/1998 |
| JP | 2000-074830 | 3/2000 |
| JP | 2000-121558 | 4/2000 |
| JP | 2001-215343 | 8/2001 |
| JP | 2002-236227 | 8/2002 |
| JP | 2003-084324 | 3/2003 |
| JP | 2003-156698 | 5/2003 |
| JP | 2003-322568 | 11/2003 |
| JP | 2004-204787 | 7/2004 |
| JP | 2004-204787 A | 7/2004 |
| JP | 2004-354671 A | 12/2004 |
| JP | 2006-522938 | 10/2006 |
| JP | 2007-534983 | 11/2007 |
| JP | 2009-515079 | 4/2009 |
| KR | 10-2006-0008314 | 1/2006 |
| WO | WO 00/28304 | 5/2000 |
| WO | WO 2004/051211 | 6/2004 |
| WO | WO 2004/090496 A2 | 10/2004 |
| WO | WO 2005/103781 A1 | 11/2005 |
| WO | WO 2007/087081 | 8/2007 |
| WO | WO 2009/061586 | 5/2009 |
| WO | WO 2010/129073 | 11/2010 |

OTHER PUBLICATIONS

International Search Report and Written Opinion from PCT/US06/60572, dated Mar. 6, 2008.

International Search Report from PCT/US2008/079962, dated Feb. 27, 2009.

Severin et al. (1989) "Bandwith and Modal Noise Effects in Fused-Head-End Multimode Fiber Passive Components" Journal of Lightwave Technology, vol. 7, No. 12, pp. 11-19.

Allen (1998) "Diode laser absorption sensors for gas-dynamic and combustion flows" Measuring Science and Technology 9:545.

Allen et al. (2002) "Tunable Diode Laser Sensing and Combustion Control" Applied Combustion Diagnostics, chapter 18.

Baer et al. (1994) "Multiplexed Diode-Laser Sensor System for

(56) References Cited

OTHER PUBLICATIONS

Simultaneous H20, 02, and Temperature Measurements" Optics Letters 19(22):1900-1902.
Docquier and Candel (2002) "Combustion control and sensors: a review" Progress in Energy and Combustion Science 28, 107-150.
Ebert et al. (1998) "Simultaneous Laser-Based in situ Detection of Oxygen and Water in a Waste Incinerator for Active Combustion Control Purposes" 27th Symposium on Combustion pp. 1301-1308.
Ebert et al. (2000) "Simultaneous Diode-Laser-Based In Situ Detection of Multiple Species and Temperature in a Gas-Fired Power Plant" Proceedings of the Combustion Institute 28:423.
Ebert et al. (2000) "The Use of Lasers as the Basis for Combustion Equipment Control" at TOTem, Intelligent Combustion Control pp. 1-15.
English translation of a Japanese Office action for corresponding JP Application No. 2007-506152.
English translation of Chinese Office action for corresponding CN Application No. 200580010448.0.
Furlong et al. (1998) "Diode Laser Sensors for Real-Time Control of Pulsed Combustion Systems": AIAA/SAE/ASME/ASEE Joint Propulsion Conference and Exhibit, pp. 1-8, 1, XP001148178.
Furlong et al. (1998) "Real-Time Adaptive Combustion Control Using Diode-Laser Absorption Sensors," 27th Symposium on Combustion pp. 103-111.
International Search Report and Written Opinion from PCT/US08/079935, dated Aug. 21, 2009.
International Search Report and Written Opinion from PCT/US10/020132, dated Oct. 8, 2010.
International Search Report and Written Opinion from PCT/US10/020345, dated Jun. 29, 2010.
International Search Report and Written Opinion from PCT/US10/045077, dated Oct. 4, 2010.
Liu et al. (2003) "Diode Laser Absorption Diagnostics for Measurements in Practical Combustion Flow Fields" 39th AIAA/ASME/SAE/ASEE Joint Propulsion Conference and Exhibit, Paper No. AIAA-2003-4581 pp. 1-6.
Miller et al. (1996) "Diode laser-based air mass flux sensor for subsonic aeropropulsion inlets" Applied Optics 35:4905.
Office Action dated Apr. 6, 2009 from the corresponding European application No. 06850383.8.
Ouyang et al. (1992) "Tomographic Absorption Spectroscopy of Combustion Gases using Tunable Infrared Diode Lasers," Paper No. 1637-20, SPIE Conference on Environmental and Process Monitoring Technologies, pp. 163-172.
Phillippe et al. (1993) "Laser diode wavelength-modulation spectroscopy for simultaneous measurement of temperature, pressure, and velocity in shock-heated oxygen flows" Applied Optics 32:6090.
Sanders et al. (2000) "Diode-Laser Sensor for Monitoring Multiple Combustion Parameters in Pulse Detonation Engines" Proceedings of the Combustion Institute 28:587.
Sanders et al. (2001) "Diode-laser absorption sensor for line-of-sight gas temperature distributions" Applied Optics 40:4404.
Settles, et al (1995) Flow Visualization VII, ed. J.P. Crowder, Begell House, NY, Sep. 1995, pp. 2-13.
Supplemental European Search Report for Application No. EP 06850383, mailed on Mar. 5, 2009.
Teichert et al. (2003) "Simultaneous in situ measurement of CO H2O, and gas temperatures in a full-sized coal-fired power plant by near-infrared diode lasers" Applied Optics 42:2043.
Upschulte et al. (1999) "Measurements of CO, CO2, OH, and H2O in room-temperature and combustion gases by use of a broadly current-tuned multisection InGaAsP diode laser" Applied Optics 38:1506.
Varghese et al. (1997) "Temperature and CO2 Concentration Profiles in Flames Measured by Laster Absorption Tomography," Paper 97-0317, AIAA 35th Aerospace Sciences Meeting, Reno, NV.
Villarreal and Varghese (2005) Applied Optics 44:6786-6795, Frequency-resolved absorption tomography with tunable diode lasers.
Webber et al. (2000) "In Situ Combustion Measurements of CO, CO2, H2O and Temperature Using Diode Laser Absorption Sensors" Proceedings of the Combustion Institute 28:407.
Wolfrum (1998) "Lasers in Combustion: From Basic Theory to Practical Devices" 27th Symposium on Combustion pp. 1-41.
International Search Report and Written Opinion from PCT/US13/032479, dated Jun. 28, 2013.

* cited by examiner

MITIGATION OF OPTICAL SIGNAL NOISE USING A MULTIMODE TRANSMIT FIBER

RELATED APPLICATIONS

This application is a 35 U.S.C. §371 national phase of PCT/US10/45077 (WO 2011/019755), filed Aug. 10, 2010, entitled "Mitigation of Optical Signal Noise Using a Multimode Transmit Fiber", which application claims the benefit of U.S. Provisional Application Ser. No. 61/232,732, filed Aug. 10, 2009, which is incorporated herein by reference in its entirety.

TECHNICAL FIELD

The present invention is directed toward monitoring of combustion processes, and more particularly toward an apparatus and method for mitigating mode or speckle pattern noise resulting from tunable diode laser absorption spectroscopy measurements associated with combustion processes.

BACKGROUND

The desirability and need to accurately measure or control combustion properties such as constituent gas concentrations and temperature resulting from the combustion of various hydrocarbons is of increasing importance in diverse fields for assuring optimum combustion conditions. The use of tunable diode laser absorption spectroscopy ("TDLAS") for combustion monitoring and control has been described with respect to coal-fired boilers and jet engines in a number of patent applications including WO 2004/090496, published Oct. 21, 2004 and entitled "Method and Apparatus for the Monitoring and Control of Combustion", WO 2005/103781, published Nov. 3, 2005, entitled "Optical Mode Noise Averaging Device", WO 2009/061586, published May 14, 2009, entitled "In Situ Optical Probe and Methods" and WO 2007/087081, published Aug. 2, 2007, entitled "Method and Apparatus for Spectroscopic Measurements in the Combustion Zone of a Gas Turbine Engine," the content of each of which is incorporated herein in its entirety for all matters that are disclosed therein. Each of the disclosed combustion monitoring apparatus and methods feature the transmission and receipt of laser light through or near a combustion zone or related gas zones. Laser spectroscopy allows the user to measure combustion properties in a measurement zone. TDLAS techniques can be implemented in situ and offer many advantages including high speed feedback suitable for dynamic process control and environmental robustness.

TDLAS is typically implemented with tunable diode lasers operating in the near-infrared and mid-infrared spectral regions. TDLAS monitoring techniques are based on a predetermined relationship between the quantity and nature of laser light received by a detector after the light has been transmitted through a region of interest and absorbed in specific spectral bands which are characteristic of the gas species resulting from combustion. The absorption spectrum received by the detector may used to determine the quantity of a gas species under analysis plus associated combustion parameters such as temperature. There are, however, technical difficulties associated with TDLAS. One of these is the need to mitigate mode and speckle noise resulting from the transmission and receipt of the laser light.

One particular area of concern is the measurement of combustion parameters in jet aircraft engines. WO 2007/087081 describes a system and method of launching and receiving a laser signal to allow the user to measure temperature downstream of the combustion zone in a gas turbine engine. In order to minimize the optical access required and thereby minimize the number of holes in the engine casing and in order to make the optical probe as robust as possible, the architecture of the probe requires that laser light emitted from the probe be reflected off a surface in the measurement zone and back to the probe. In certain applications, to minimize the risk of misalignment, the reflecting surface is treated to provide for a Lambertian reflection. Such a surface is referred to herein as a "Lambertian surface." For example, in those instances where the probe is reflecting light off an internal engine surface, such as an inner casing, a turbine blade or turbine shaft, the internal engine surface may be covered with a relatively rough thermal barrier coating which provides the Lambertian reflection. Lambertian reflection scatters light at the time of the reflection. Although Lambertian reflection can greatly decrease the signal levels available for detection, it also reduces alignment sensitivity since the light is scattered more or less equally into a half sphere of $\Pi$ steradians.

In addition to the reduced signal level, reflection from a Lambertian surface causes an additional difficulty with regard to the signal to noise ratio of the measurement. Laser speckle noise appears in the reflected/scattered signal causing time-dependent undulating waves in the wavelength spectrum received from the laser. This makes fitting an absorption spectrum to the signal very difficult and subject to error. In the case of reflection received from a Lambertian (roughened) surface, the speckle noise is an interference phenomenon substantially similar in cause and effect to mode noise created within a multimode fiber. Light reflected from the Lambertian surface travels different distances in order to reach the receiving optic. When light waves on a first path interfere with those on another path, it causes fluctuating regions of high and low intensity creating the time-dependent undulating waves in the spectrum. These waves make it difficult to distinguish absorption of the wavelengths of interest by monitored gases from losses associated with speckle noise.

Various embodiments disclosed herein are intended to overcome one or more of the problems discussed above or other mode noise problems in TDLAS detection apparatus and methods.

SUMMARY OF THE EMBODIMENTS

A first embodiment comprises an apparatus for measuring combustion parameters in the measurement zone of a gas turbine engine. The measurement zone is defined as being between an outer casing and an engine component having a reflecting surface inside the outer casing. The apparatus comprises a laser generating a transmitting beam of light of a select wavelength and a multimode transmitting fiber optically coupled to the laser. A transmitting optic is optically coupled to the multimode optical fiber for transmitting the beam into the measurement zone. The reflecting surface is configured to provide a Lambertian reflection. A receiving optic is positioned to receive the Lambertian reflection. Means are provided in operative association with the multimode transmitting fiber for averaging modal noise induced signal level variation of light propagating within the multimode transmitting fiber.

In one embodiment, the transmitting optic and the receiving optic are the same optic and the multimode optical fiber acts as both a transmitting fiber and a receiving fiber. Such an embodiment further comprises means optically coupled to the multimode optical fiber for separating the received beam from the transmitting beam. The means for averaging may comprise a means for cyclically varying an index of refraction of the multimode optical fiber over a select period of time or means for scrambling a light distribution within the multimode optical fiber. The means for averaging may comprise means for cyclically varying the temperature of the multimode optical fiber or means for cyclically manipulating the multimode optical fiber. The means for cyclically manipulating the multimode optical fiber may comprise an apparatus configured to twist a portion of the multimode optical fiber, stretch the multimode optical fiber or shake or vibrate a portion of the multimode optical fiber.

Another embodiment is a gas turbine engine comprising a combustion zone between an outer casing and a surface within the casing. A port is provided in the outer casing operatively associated with the zone and the port is optically associated with a reflective surface. A transmitting and receiving optic is optically coupled with the port and the transmitting and receiving optic is configured to transmit a beam to the reflective surface and to receive at least a portion of the beam reflected off of the reflective surface. A multimode optical fiber is optically coupled to the transmitting and receiving optic. Means are provided in operative association with at least a portion of the multimode optical fiber for averaging modal noise induced signal level variation of light propagating within the multimode optical fiber. The means for averaging may be any of those means discussed above with respect to the first embodiment. As with the first aspect of the invention, the reflective surface may have a Lambertian coating. The Lambertian coating may be a thermal barrier coating.

Another embodiment is a method of measuring a combustion property within a zone of a gas turbine engine. The method comprises transmitting a beam of light at a select wavelength through a multimode optical fiber into the zone. The beam is reflected off of a surface in the zone. The beam is received with a receiving optic. The method further includes averaging modal noise induced signal level variation within the beam of light propagating within the multimode optical fiber. The receiving optic may be optically coupled to the multimode optical fiber and further function as a transmitting and receiving optic. A Lambertian dispersion surface may be provided on the reflective surface.

Yet another embodiment is a method of measuring a property within a zone. The method comprises transmitting a beam of laser light of a select wavelength through a multimode optical fiber and through a transmit optic optically coupled to the zone. At least a portion of the transmitted beam is received by a receiving optic optically coupled to the transmit optic. The method further includes averaging modal noise induced signal level variation of the beam of light propagating within the multimode optical fiber. The method may comprise the transmitting optic and the receiving optic being the same optic. The method may further comprise the multimode optical fiber carrying the transmitted beam and the at least a portion of the beam received with the receiving optic. The method may further comprise separating the at least a portion of the received beam from the transmitted beam. The step of averaging mode noise induced signal variations may be performed by cyclically manipulating the multimode optical fiber. The cyclical manipulation may include twisting the multimode optical fiber, stretching the multimode optical fiber, shaking the multimode optical fiber, vibrating the optical fiber or combinations thereof.

DETAILED DESCRIPTION

Figure 1:
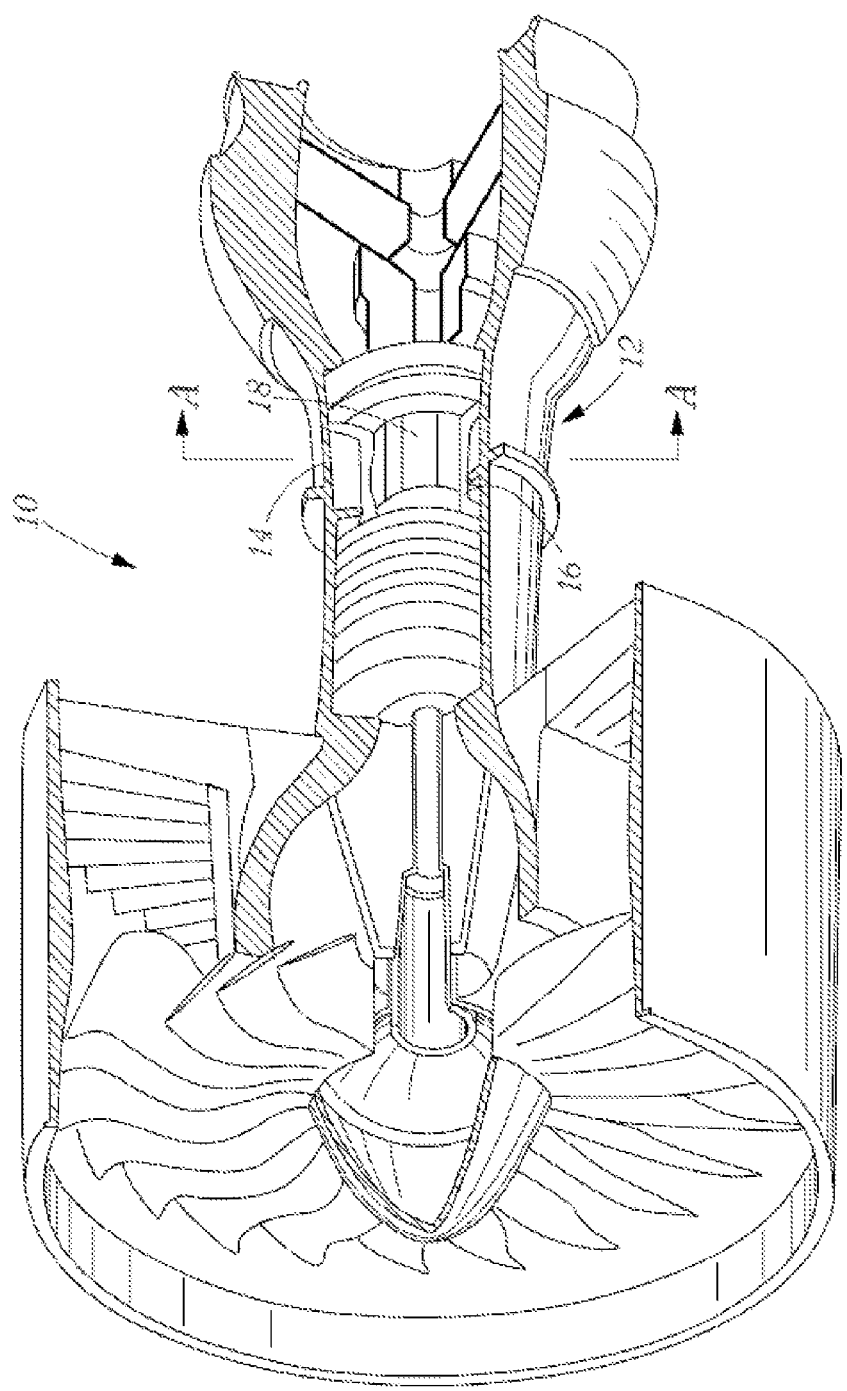
FIG. 1 is a partial sectional view taken along a lengthwise axis of a schematic representation of a gas turbine engine.

Unless otherwise indicated, all numbers expressing quantities of ingredients, dimensions, reaction conditions, and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

A. Tunable Diode Laser Absorption Spectroscopy

TDLAS is performed by the transmission of laser light through a target environment, followed by the detection of the absorption of the laser light at specific wavelengths, due to absorption by target gases such as oxygen. Spectral analysis of the detected light allows identification of the type and quantity of gas along the laser path as well as the determination of properties such as temperature and pressure. The non-contact nature of laser absorption spectroscopy makes it well suited for harsh environments such as the combustion zone of a gas turbine engine, or flammable or toxic environments where other probes cannot be used. The use of laser light provides the high brightness necessary to receive detectable transmission in the presence of severe attenuation that may be seen in some of these environments. To better withstand the harsh conditions of the target applications, the laser light may be brought in to the target environment through armored optical fiber.

Effective sensing of temperature or the concentration of multiple combustion process component gasses requires the performance of TDLAS with multiple widely spaced frequencies of laser light. The frequencies selected must match the absorption lines of the transitions being monitored. The use of a multiplexed probe beam can allow for the simultaneous monitoring of more than one combustion gas species, allowing for more refined control over a combustion process.

B. Mode Noise

The optical train of a TDLAS system presents many design challenges due to the opposing design requirements of the reduction of mode noise and high efficiency light collection. Mode noise and the resulting changes in a speckle pattern are defined herein as two separate but related phenomenon: First, mode noise is a change in the signal level of detected light that results from non-uniform time and wavelength varying light distribution in the core of a fiber used to collect and transport the light to and from the zone being probed. Second, a mode noise like interference based speckle pattern may also occur when light is reflected and transmitted in free space. In particular, mode noise may occur in light reflected from a Lambertian reflecting surface because light reflected from the surface travels different distances in order to reach the receiving optic. This results in the development of laser speckle noise in the reflected signal, causing time-dependent undulating waves in the received spectrum. The general discussion of mode noise below is equally applicable to mode noise created in a multimode fiber or speckle pattern noise created in a reflected signal in free space.

In a multimode fiber, different modes may propagate at different velocities due to refractive index variations. The intensity distribution in the fiber is then a speckle pattern resulting from interference of all the propagating modes that have undergone different effective path lengths. If all light in the speckle pattern is collected and detected, then constructive and destructive interference cancel exactly and the total transmitted power does not depend on wavelength or fiber length. If clipping, vignetting or other loss is introduced, the exact cancellation fails and the detected power changes with wavelength and/or time. In a TDLAS sensing system the power changes resulting from mode noise are quite problematic. Certain spectroscopy techniques rely on absorption of specific wavelengths of light by the gas species being studied. The absorptions are detected by a decrease in power at the critical wavelength. Thus, mode noise can mimic the power drop associated with absorption and obscure the data collected through TDLAS.

C. Representative Probe Configurations

WO 2007/087081, WO 2009/061586, U.S. patent application Ser. No. 12/359,900, filed Jan. 26, 2009, entitled, "Alignment Free Single-Ended Optical Probe and Methods for Spectroscopic Measurements in a Gas Turbine Engine" each describe embodiments of TDLAS devices or probes for monitoring combustion processes. Each of these applications is incorporated herein in their entirety for all matters disclosed therein. In each of the embodiments described in these applications, a single-mode optical fiber is used on the transmit side of the probe to convey laser light of select wavelengths to the transmit optic. Single mode fibers were used in these various embodiments to minimize mode noise that would otherwise result from the use of a multimode optical fiber on the transmit side. In an alternative embodiment, as described in WO 2005/103781 which application is incorporated herein in its entirety for all matters disclosed therein, a very short length of multimode optical fiber is used immediately adjacent the transmit optic. The mode noise reduction strategies and apparatus disclosed herein are applicable to the probe configurations disclosed in the references incorporated herein and similar probe configurations.

Figure 2:
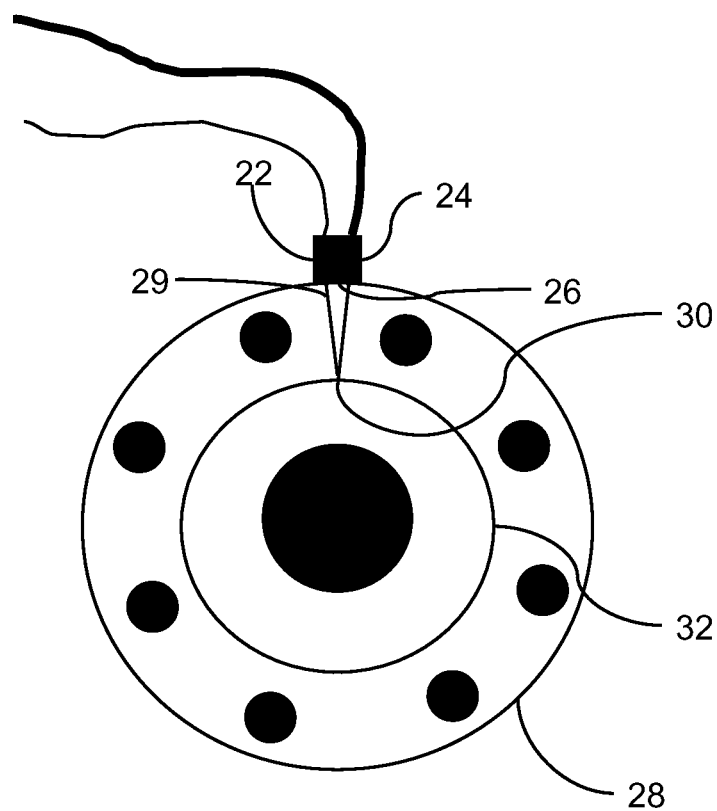
FIG. 2 is a schematic cross-sectional view of the combustion zone of the gas turbine engine of FIG. 1 taken along lines A-A of FIG. 1 illustrating one potential optical coupling of a transmitting/receiving optic pair.
Figure 3:
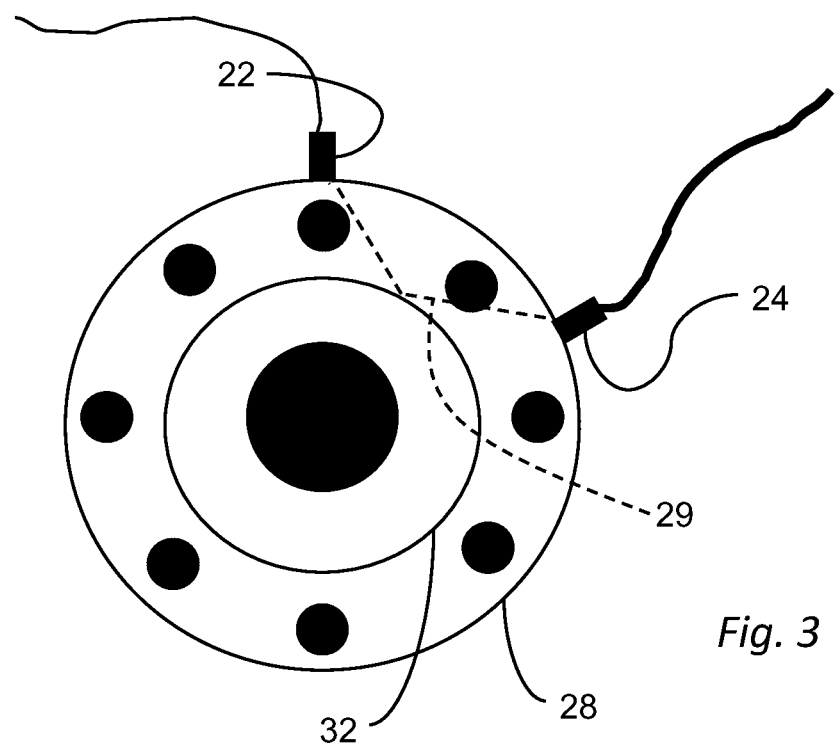
FIG. 3 is similar to FIG. 2 only illustrating a second potential coupling of a transmitting/receiving optic pair.

On representative type of probe suitable for enhancement with the disclosed embodiments is shown in FIGS. 1 and 2. FIG. 1 depicts in schematic form a partial sectional view taken along an axis of a gas turbine engine 10 illustrating the combustion chamber 12. FIG. 2 is a cross-section view taken along lines A-A of FIG. 1 illustrating in schematic form the operative association of a transmitting optic 22 and a receiving optic 24 pair. In the embodiment illustrated in FIG. 2, the transmitting/receiving optics pair 22, 24 are optically coupled to a port 26 in an outer casing 28 and physically secured to the outer casing. The port 26 may be a borescope port which is a penetration in the outer casing available near the combustion zone on many modern gas turbine engines. The borescope ports are intended to allow observations of the turbine blade during servicing, but are further intended to be accessible only when the engine is not running. Thus, these ports typically are plugged during engine operation. The transmitting/receiving optics pair 22, 24 are secured to the port 26 and the outer casing in a manner enabling them to function as the plug they replace. The transmitting/receiving optics pair 22, 24 are configured for operative association with the port 26 in the outer casing of the gas turbine so that the transmitting optic and the receiving optic are optically coupled by reflecting a probe beam 29 off a portion 30 of the inner casing 32 substantially opposite the port 26. In alternative embodiments, the reflecting surface can be a separate engine structure such as a turbine blade, a dedicated reflector or any other structure that serves to reflect the beam 28 between the optic pairs 22 and 24. Also, although the optic pairs 22, 24 are shown as being placed together at a single port in the FIG. 2 embodiment, the optics may be spatially separated. Thus, in an alternative embodiment illustrated in FIG. 3, the transmitting optic 22 may direct the beam 29 illustrated in phantom lines off the inner casing to a receiving optic 24 associated with a distinct port. In such an embodiment the portion of the inner casing 32 (or other structure) upon which the beam is reflected would be between the transmitting/receiving optics 22, 24.

D. Mode Noise Reduction

As described above, known embodiments of probes typically include a single mode fiber on the transmit side of a probe system to minimize mode noise. Surprisingly, the inventors have found that if steps are taken to average modal noise induced signal level variation of light propagating within a multimode optical fiber, a multimode optical fiber can be used on the transmit side in the various embodiments of the optical probes disclosed above. Mode noise reduction in the transmitting multimode fiber certainly helps to limit mode noise generated therein, but also can help to minimize the mode noise generated upon reflection of the signal from a Lambertian surface as described below.

Figure 4:
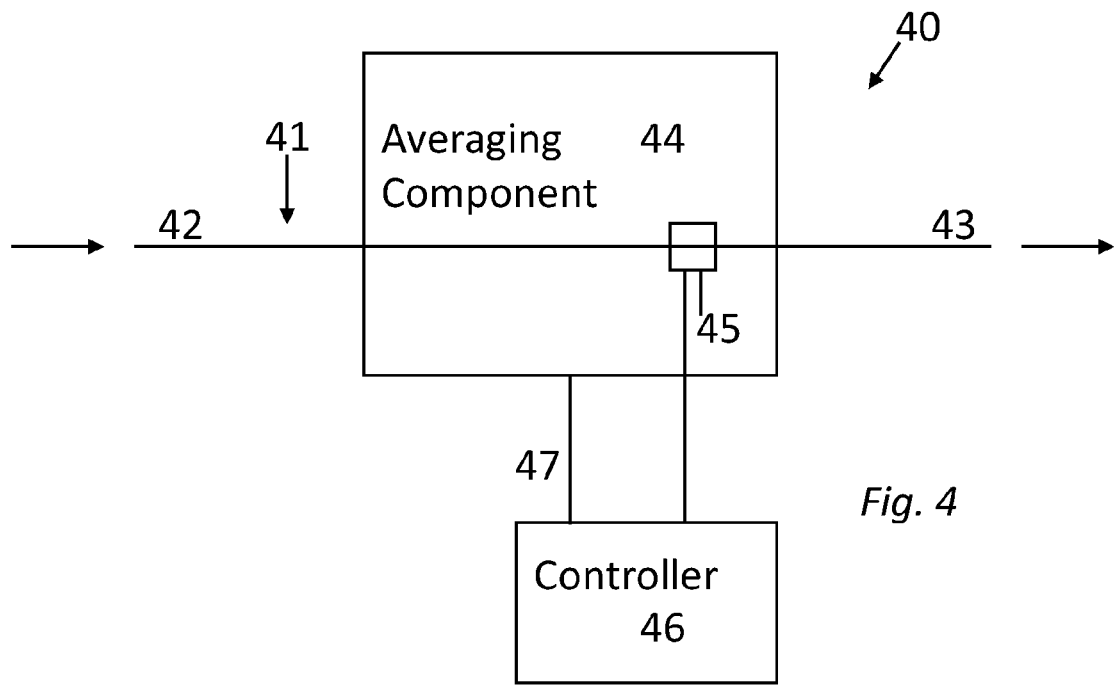
FIG. 4 is a schematic representation of a mode noise reduction device that may be associated with a portion of a multimode optical fiber.

Mode noise may addressed at the multimode transmit fiber in various manners as more particularly described in WO 2005/103781 which application is incorporated in its entirety herein for all mode noise reduction strategies disclosed therein. For example, as shown schematically in FIG. 4, the cyclical phase shifting or scrambling of modal noise to produce a time averaged measurement may be accomplished with an optical device 40. The optical device 40 will include a multimode optical fiber 41 having an input 42 and an output 43. Light may be coupled to the input 42 of the multimode optical fiber 41 and will generally propagate through the system in the direction of the arrows shown in FIG. 4 in association with the input 42 and the output 43.

The optical device 40 will also include an averaging component 44 operatively associated with the multimode fiber 41. The averaging component 44 may include apparatus for cyclically varying an index of refraction of the multimode optical fiber 41 over a select period of time. Alternatively or in addition, the averaging component 44 may include an apparatus for scrambling a light distribution within the multimode optical fiber 41. Variation of an index of refraction or scrambling a light distribution may be accomplished by the averaging component 44 through cyclically varying the temperature of the multimode optical fiber 41, cyclically manipulating the multimode optical fiber 41, or both.

In an embodiment where the averaging component 44 performs a cyclical manipulation of the multimode optical fiber 41, the averaging component 44 may twist, stretch, vibrate or shake a portion of the multimode optical fiber 41. In an embodiment where the averaging component 44 cyclically varies the temperature of the multimode optical fiber 41, various thermal elements or thermal components may be provided in thermal communication with a portion of the multimode optical fiber. Any apparatus which will affect the temperature of the multimode optical fiber 41 can be included in the averaging component 44. Representative devices which can be used to affect the temperature of the multimode optical fiber 41 include a thermoelectric module, a resistive heater, an infrared heater, a chemical heater, a conventional refrigeration device utilizing compressed fluids and heat exchangers, a chemical cooler, a source of fluid cooled below ambient temperature, and a source of fluid heated above ambient temperature.

In an embodiment where the averaging component 44 causes cyclic heating or cooling of the multimode fiber 41, a sensor 45 may also be placed in thermal communication with the multimode optical fiber 41. The sensor 45 may provide information to a controller 46 which in turn may control the averaging component 44 through a control line 47.

It is important to note that the embodiments disclosed herein may utilize any type of mode noise averaging component in association with a multimode fiber. The device 40 described above is therefore merely a representative types of mode noise averaging device. The embodiments disclosed herein may be implemented with the described or any other type of mode noise averaging device.

Figure 5:
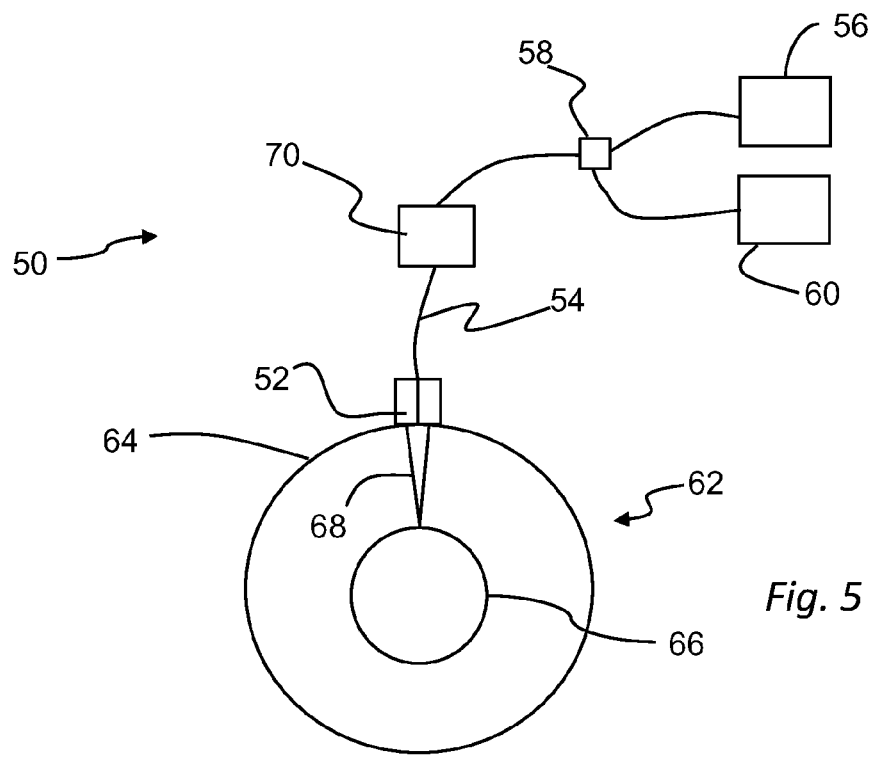
FIG. 5 is a view of a combustion zone sensing device as disclosed herein, featuring mode noise mitigation.

As described above, one useful probe includes a TDLAS sensor used to sense or control processes within a jet engine. Such a sensing system is particularly vulnerable to mode noise created within a multimode fiber or created in free space when the probe beam is reflected, for example off of a Lambertian reflecting surface. FIG. 5 is a schematic illustration of a first embodiment of a TDLAS sensor 50. The TDLAS sensor 50 comprises a transmit and receive optic 52 which may include, for example, several optical components such as one or more lenses. The transmit and receive optic 52 may be monolithic. Alternatively the transmit and receive optic 52 may have separate transmission and reception optical components.

A multimode optical fiber 54 is optically coupled to the transmit and receive optic 52. The multimode optical fiber 54 is further optically coupled to a tunable diode laser 56 which produces a beam of light at a select wavelength. In one embodiment, an optical divider 58 is optically associated with the multimode optical fiber 54. The optical divider 58 may be, by way of example, a spatial multiplexer or a circulator of the type used in telecommunications applications. The function of the optical divider 58 is to divide optical signals received by the transmit and receive optic 52 from an optical signal generated by the tunable diode laser 56 and to deliver the received portion of the signal to a detector 60, which is typically a photo detector sensitive to the frequency of light generated by the tunable diode laser 56. In selected embodiments, the TDLAS sensor 50 is operatively associated with a portion of a gas turbine engine 62 with a portion of the gas turbine engine 62 including an outer casing 64 and an internal component 66 which may be, for example, an engine component such as inner casing, a turbine shaft, a turbine blade or any other component found within the outer casing of a gas turbine engine or a dedicated reflecting surface.

In most applications the sensing apparatus will be associated with a portion of the gas turbine engine at or downstream of the combustion zone of the gas turbine engine for the purpose of measuring gases associated with combustion within the engine and determining properties such as temperature. A probe beam 68 generated by the tunable diode laser 56 is directed off the internal component 66 so that it reflects back to the transmit and receive optic 52 as illustrated in FIG. 5. A portion of the transmitted beam received by the transmit and receive optic 52 is conveyed by the multimode optical fiber 54 to the optical divider 58 for detection by the detector 60.

In order to maintain optical alignment between the transmit and receive optic 52 and the internal component 66, it may be desirable to provide a Lambertian surface on a portion of the interior component 66 reflecting the beam 68. Lambertian reflection occurs when the incident beam is scattered such that the apparent brightness of the beam on the reflective surface is approximately the same to an observer regardless of the observer's angle of view. Thus, Lambertian reflection is a diffuse reflection. While Lambertian reflection will tend to decrease the intensity of the reflected beam, Lambertian reflection will also tend to overcome minor misalignments between transmit and receive optic 12 and the internal reflection surface 66. Lambertian reflection may be achieved by bead blasting, sanding, painting or otherwise treating the reflective surface to provide for a diffuse reflection. Specifically, a rough thermal barrier coating as is often provided on interior components of a gas turbine engine can produce such a Lambertian reflection.

Signal mode noise from the Lambertian surface results when light reflected from the surface travels different distances in order to reach the receive optic. This results in the development of laser speckle noise in the reflected signal, causing time-dependent undulating waves in the received wavelength spectrum of the laser. An averaging component 70 of the type discussed above may be operatively associated with the multimode optical fiber 54. As described above, the purpose of the averaging component 70 is to average modal noise induced signal level variation of light propagating within the multimode optical fiber 54. In one embodiment, the averaging component 70 is a mechanical vibrator. Surprisingly, mechanical vibration of the multimode optical fiber 54 has been found to substantially mitigate speckle noise resulting from reflection of the beam off a Lambertian surface. In one embodiment, use of a multimode optical fiber 54 having a 200 micron core which is subject to mechanical vibration has been shown to nearly eliminate speckle noise when vibration of the fiber 54 and therefore, averaging of the single, occurs over a 0.05 second vibration cycle. One example of a suitable optical fiber 54 is a FIBERGUIDE AFS 200/220Z.

Figure 6:
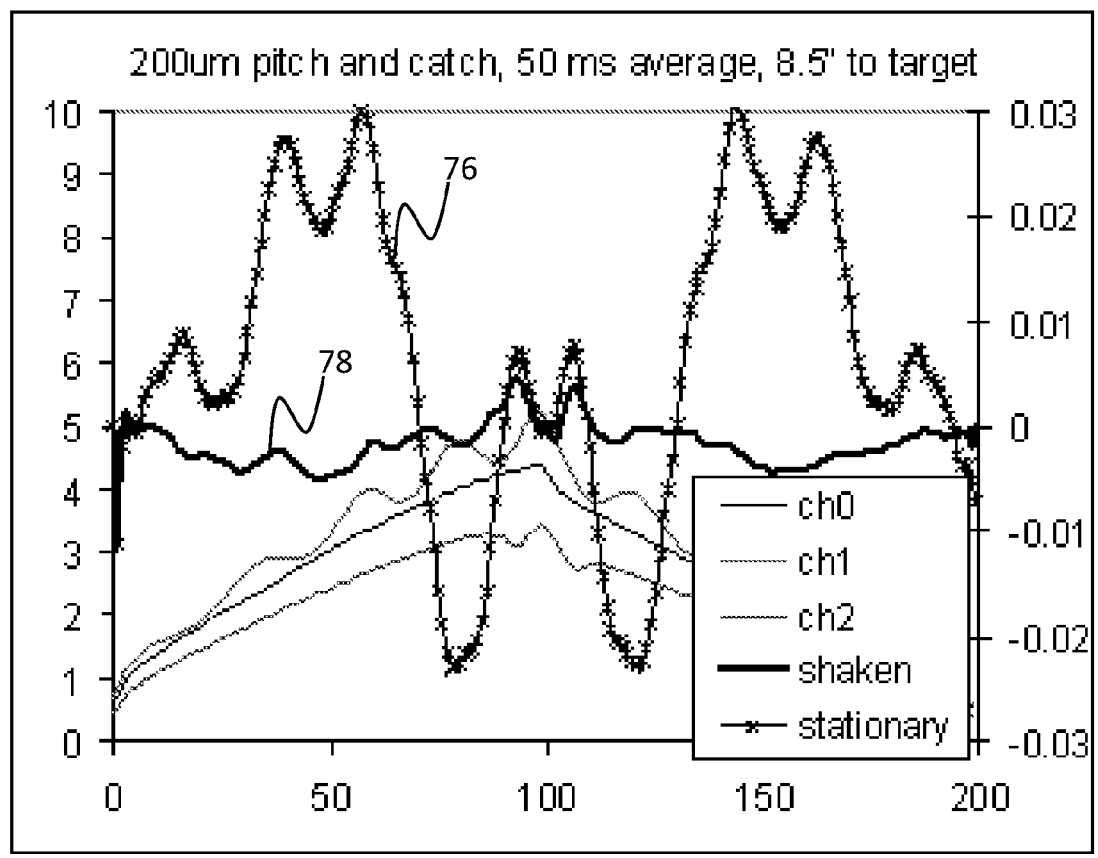
FIG. 6 is a graphic representation of mode nose reduction achieved utilizing the methods disclosed herein.

FIG. 6 graphically illustrates the mode noise reduction achieved as described above. As shown in FIG. 6, the signal 76 received by a stationary multimode optical fiber has extreme peaks and valleys. With the 200 micron fiber mechanically shaken or vibrated, the speckle noise is a reduced by a factor of roughly 20 with 0.05 second cycle of vibration averaging, resulting in the substantially smoother signal 78.

The embodiment illustrated in FIG. 5 could be altered by providing spatially separate transmitting and receive optics optically communicating with each other by reflection of the transmit beam off of an intermediate reflective surface within the engine. In this alternative, a multimode transmit optical fiber may be optically coupled to the transmit optic and a multimode optic receive fiber may be coupled to the receiving optic. In such an embodiment an averaging component could be operatively associated with only the transmit optical fiber or with both the transmit multimode optical fiber and the receive multimode optical fiber. Furthermore, as discussed above, various other embodiments of sensing apparatus could employ an averaging component operatively associated with a transmitting multimode optic fiber to improve signal quality.

An alternative embodiment is a method of measuring a combustion property within a zone of a gas turbine engine. The method comprises transmitting a beam of light at a select wavelength through a multimode optical fiber into the zone. The beam is reflected off of a surface in the zone. The beam is received with a receiving optic. The method further includes averaging modal noise induced signal level variation within the beam of light propagating within the multimode optical fiber. The receiving optic may be optically coupled to the multimode optical fiber and further function as a transmitting and receiving optic. A Lambertian dispersion surface may be provided on the reflective surface.

Yet another alternative embodiment is a method of measuring a property within a zone. The method comprises transmitting a beam of laser light of a select wavelength through a multimode optical fiber and through a transmit optic optically coupled to the zone. At least a portion of the transmitted beam is received by a receiving optic optically coupled to the transmit optic. The method further includes averaging modal noise induced signal level variation of the beam of light propagating within the multimode optical fiber. The method may comprise the transmitting optic and the receiving optic being the same optic. The method may further comprise the multimode optical fiber carrying the transmitted beam and the at least a portion of the beam received with the receiving optic. The method may further comprise separating the at least a portion of the received beam from the transmitted beam. The step of averaging mode noise induced signal variations may be performed by cyclically manipulating the multimode optical fiber. The cyclical manipulation may include twisting the multimode optical fiber, stretching the multimode optical fiber, shaking the multimode optical fiber, vibrating the optical fiber or combinations thereof.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. An apparatus for measuring a combustion parameter in a zone, the apparatus comprising:
    a laser generating a transmit beam of light of a select wavelength;
    a multimode transmitting optical fiber optically coupled to the laser;
    a transmitting optic optically coupled to the multimode transmitting optical fiber for transmitting the transmit beam into the zone;
    a reflecting surface in the zone;
    a receiving optic positioned to receive a reflection of the transmit beam from the reflecting surface;
    wherein the transmitting optic and the receiving optic are the same optic; and
    means operatively associated with the multimode transmitting optical fiber for averaging modal noise induced signal level variation of light propagating within the multimode transmitting optical fiber.

2. The apparatus of claim 1 wherein the multimode transmitting optical fiber also functions as a receiving optical fiber.

3. The apparatus of claim 2 further comprising means optically coupled to the multimode transmitting optical fiber for separating the received beam from the transmitting beam.

4. The apparatus of claim 3 wherein the means for separating comprises one of a spatial multiplexer and a circulator.

5. The apparatus of claim 1 further comprising the reflecting surface being configured to provide a Lambertian reflection.

6. The apparatus of claim 1 wherein the means for averaging comprises one of:
    means for cyclically varying an index of refraction of the multimode optical fiber over a select period of time; and
    means for scrambling a light distribution within the multimode optical fiber.

7. The apparatus of claim 1 wherein the means for averaging comprises an apparatus configured to perform at least one of:
    cyclically varying the temperature of the multimode optical fiber;
    twisting the multimode optical fiber;
    stretching the multimode optical fiber;
    shaking the multimode optical fiber; and
    vibrating the multimode optical fiber.

8. The apparatus of claim 1, wherein the zone is a measurement zone of a gas turbine engine, the measurement zone being defined as being between an outer casing of the engine and an engine component having a reflecting surface inside the outer casing.

9. An apparatus for measuring a combustion parameter in a zone, the apparatus comprising:
    a laser generating a transmit beam of light of a select wavelength;
    a multimode optical fiber optically coupled to the laser;
    a transmitting/receiving optic optically coupled to multimode optical fiber; and
    a reflecting surface in the zone, the reflecting surface being constructed and arranged to reflect at least a portion of the transmit beam transmitted from the transmitting/receiving optic back to the transmitting/receiving optic;
    wherein the multimode optical fiber carries both the transmit beam and the at least a portion of the transmitted beam reflected back to the transmitting/receiving optic; and
    wherein the transmitting/receiving optic is configured to transmit the transmit beam into the zone, and receive the at least a portion of the transmitted beam reflected from the reflecting surface.

10. The apparatus of claim 9 further comprising means optically coupled to the multimode optical fiber for separating the at least a portion of the transmitted beam reflected back to the transmitting/receiving optic from the transmit beam.

11. The apparatus of claim 10 wherein the means for separating comprises one of a spatial multiplexer and a circulator.

12. The apparatus of claim 9 further comprising the reflecting surface being configured to provide a Lambertian reflection.

13. The apparatus of claim 9 further comprising means operatively associated with the multimode optical fiber for averaging modal noise induced signal level variation of light propagating within the multimode optical fiber.

14. A method of measuring a property within a zone, the method comprising:

transmitting a beam of light of a select wavelength through a multimode optical fiber and a transmit optic optically coupled to the zone;
reflecting at a reflecting surface at least a portion of the transmitted beam to a receiving optic;
receiving from the reflecting surface a reflection of the at least a portion of the transmitted beam with the receiving optic optically coupled to the transmit optic;
the transmitting optic and the receiving optic being the same optic; and
averaging modal noise induced signal level variations of the beam of light propagating within the multimode optical fiber.

15. The method of claim 14 further comprising the multimode optical fiber carrying the transmitted beam and the at least a portion of the received beam.

16. The method of claim 15 further comprising separating the at least a portion of the received beam from the transmitted beam.

17. The method of claim 16 further comprising detecting the strength of the at least a portion of the received beam.

18. The method of claim 14 wherein the step of averaging modal noise is performed by cyclically manipulating the multimode optical fiber.

19. The method of claim 14 further comprising reflecting the transmitted beam off a surface in the zone to the receiving optic.

20. The method of claim 19 further comprising providing a Lambertian dispersion of the transmitted beam at the surface in the zone.

* * * * *